United States Patent [19]
Wirth et al.

[11] Patent Number: 5,292,885
[45] Date of Patent: Mar. 8, 1994

[54] PYRANONE, PROCESS FOR ITS PREPARATION, ITS USE IN THE PREPARATION OF A NEW PYRIDINONE AND A PROCESS FOR THE PREPARATION OF SAME

[75] Inventors: Didier G. Wirth, Paris; Dominique Gibert, Villers; Laurence Ferrucio, Paris, all of France

[73] Assignee: Isochem, Paris, France

[21] Appl. No.: 565,835

[22] Filed: Aug. 13, 1990

[30] Foreign Application Priority Data

Aug. 11, 1989 [FR] France ................... 89 10831

[51] Int. Cl.$^5$ ............... C07D 213/08; C07D 213/28; C07D 315/00
[52] U.S. Cl. ................... 546/250; 546/290; 549/417
[58] Field of Search ............... 546/290, 250; 549/417; 568/415, 17

[56] References Cited

U.S. PATENT DOCUMENTS

| | | | |
|---|---|---|---|
| 4,171,318 | 10/1979 | Chan et al. | 568/415 |
| 4,590,299 | 5/1986 | La Mattina et al. | 568/415 |
| 4,603,144 | 7/1986 | Campbell et al. | 549/417 |
| 4,705,871 | 11/1987 | Masatera et al. | 549/417 |
| 4,876,393 | 10/1989 | Heine et al. | 568/415 |

OTHER PUBLICATIONS

Tetrahedron Letters No. 25, pp. 1939–1942, 1976, "Photoisomerization of 4-Pyrones, Nucleophilic Trapping of Reactive Intermediates".
Chemical and Engineering News, Jan. 30, 1989, p. 2.
E. Earl Royals and Kent C. Brannok, J.A.C.S., 75, p. 2050 (1952).
Shobha Mishra and R. D. Shrivastava, J. Ind. Chem. Soc., 1978, p. 1273.

Primary Examiner—C. Warren Ivy
Assistant Examiner—Raymond Covington
Attorney, Agent, or Firm—Sughrue, Mion, Zinn, Macpeak & Seas

[57] ABSTRACT 2,3,5-(4H)-Trimethyl pyranone having the formula:

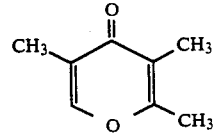

which is prepared by acetylation of a ketone derived from 2-formyl-3-pentanone and preparation of 2,3,5-(1H)-trimethyl 4-pyridinone having the formula:

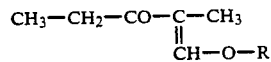

by ammonolysis of the 2,3,5-(4H)-trimethyl 4-pyranone.

8 Claims, No Drawings

PYRANONE, PROCESS FOR ITS PREPARATION, ITS USE IN THE PREPARATION OF A NEW PYRIDINONE AND A PROCESS FOR THE PREPARATION OF SAME

The present invention relates to 2,3,5-(4H)-trimethyl 4-pyranone, to a process for its preparation, to its use in the preparation of 2,3,5-(1H)-trimethyl 4-pyridinone, and to a process for the preparation of 2,3,5-(1H)-trimethyl 4-pyridinone using 2,3,5-(4H)-trimethyl 4-pyranone.

An object of the present invention, therefore, is 2,3,5-(4H)-trimethyl 4-pyranone, as well as a process enabling its preparation under good conditions and with a good yield.

A further object of the invention is the use of 2,3,5-(4H)-trimethyl 4-pyranone in the preparation of 2,3,5-(1H)-trimethyl using ammonolysis.

Finally, an object of the present invention is a process for the industrial synthesis of 2,3,5-(1H)-trimethyl 4-pyridinone, which is a new compound useful as a manufacturing intermediate for pharmaceutical products.

Several anti-ulcer agents, such as Omeprazole, contain in their formulae a moiety derived from a 4-alkoxy-2,3,5-trimethyl-pyridine (I):

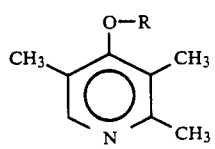

in which R designates an alkyl group containing 1 to 3 carbon atoms, possibly substituted by one or more halogens.

The conventional synthesis of these intermediates calls for the nitration of the trimethylpyridine N-oxide, which operation is known to be dangerous (see, for example: *Chem. & Eng. News*, Jan. 30, 1989, page 2).

4-Alkoxy-2,3,5-trimethyl-pyridines of general formula (I) can be considered to be functional derivatives of 2,3,5-trimethyl 4-pyridinol or 2,3,5(1H)-trimethyl 4-pyridinone, tautomeric forms in accordance with formula (II):

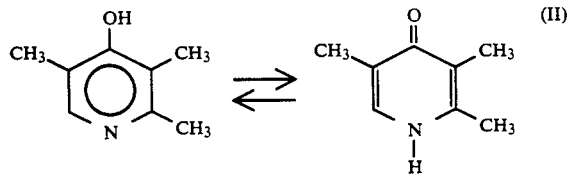

Curiously enough, this compound is not disclosed in the literature and the present invention specifically provides an industrial synthesis of this new intermediate, which is simple and without danger.

In accordance with the present invention, the 2,3,5-(1H)-trimethyl 4-pyridinone is prepared in two steps from a derivative of 2-formyl-3-pentanone having general formula (III)

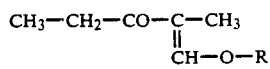

in which R designates a hydrogen atom, an alkali metal atom, an alkyl group containing from 1 to 8 carbon atoms or even an acetyl radical, any of which may possibly be substituted with one or more halogen atoms.

In a first stage, the action of an acetylating agent on the ketones of general formula (III) leads to 2,3,5-(4H)-trimethyl pyranone having formula (IV):

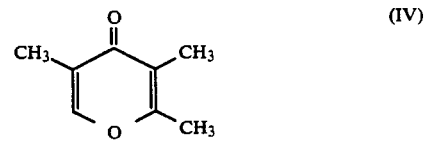

which is a new compound entering into the framework of the present invention.

In a second stage, the action of ammonia on the pyranone of formula (IV) quesi-quantitatively provides the pyridinone of formula (II):

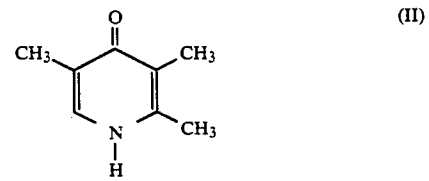

which the person skilled in the art can transform as he likes into the intermediate: for example, chloro trimethyl pyridine, methoxy trimethyl pyridine, or others.

Starting materials, which correspond to general formula (III), are known and easily accessible (see, for example: K. C. Brannok, *J.A.C.S.*, 75, p. 2050, and R. D. Shrivastave, *J. Ind. Chem. Soc.*, 1978, p. 1273). They are generally obtained by formylation of the diethyl ketone using an alkyl formate such as methyl formate or ethyl formate, in the presence of an alkaline alcoholate such as sodium or potassium methylate, or even sodium ethylate.

The 2-formyl-3-pentanone salts obtained in this manner can then be converted by acidification to free 2-formyl-3-pentanone or to enol ethers of same through the action of an alcohol in an anhydrous acid medium or through the action of an alkylating agent, such as methyl or ethyl sulfates and halides such as methyl, ethyl, or isopropyl chloride, bromide or iodide, or others.

The action of an acetylating agent, such as acetyl chloride, acetic anhydride or isopropenyl acetate results in the derivative corresponding to general formula (III) in which R is an acetyl group.

The acetylation of the ketones corresponding to new general formula (III) can be achieved using an agent such as acetic anhydride, acetyl chloride or acetyl bromide in the presence of a Lewis acid such as boron trifluoride or aluminum, cobalt or zinc halides or even a base such as alkaline amidides or alcoholates. This is preferably done at low or moderate temperature, between $-40°$ C. and $+30°$ C.

2,3,5-(4H)-trimethyl 4-pyranone can be isolated after redissolving the reaction mixture in water and can be purified by distillation or recrystallization in a solvent such as hexane or heptane.

The final ammonolysis is preferably carried out between $100°$ C. and $150°$ C. under an ammonia pressure of 5 to 15 bars, for example in an aqueous or hydroalcoholic medium. The trimethyl pyridone, which is slightly soluble in aprotic solvents, crystallizes easily.

The following examples, given by way of example, of one embodiment will further illustrate the invention without, however, limiting the scope thereof

EXAMPLE 1

2,3,5-(4H)-Trimethyl 4-pyranone 48 g of boron trifluoride were absorbed by a mixture of 36 g of acetic acid and 15.5 g of acetic anhydride, then a mixture of 15.5 g of acetic anhydride and 19.2 g of 1-methoxy-2-methyl-1-pentene-3-one were poured into the suspension thus obtained. After three days of stirring at 25° C., then hydrolysis followed by extraction using methylene chloride, washing to neutrality and concentration of the organic phase, 7.7 g of crude trimethyl pyranone were obtained distilling around 80° C. under 1 mm of mercury.

After recrystallization in heptane, the product melted at 34° C.

The NMR spectrum of the proton (CDC13) showed 4 signals to appear: 3H at $\delta = 1.91$ ppm (doublet); 3H at $\delta = 1.95$ ppm (singlet); 3H at $\delta = 2.27$ ppm (singlet); 1H at $\delta = 7.59$ ppm (multiplet).

EXAMPLE 2

2,3,5-(1H)-Trimethyl 4-pyridinone 1 part by weight of the trimethyl pyranone obtained in accordance with Example 1 and 10 parts by weight of a 20% aqueous ammonia solution were placed in a stainless steel autoclave and then kept at 125° C. for 24 hours: the pressure reached 14.5 bars.

After cooling and concentration until dry, then dissolving the residue in acetone and filtration, the desired pyridone was obtained with a yield of 92%.

Melting point: 17° C.

NMR spectrum of the proton (DMSO D 6): 6H $\delta = 1.825$ ppm (2 singlets); 3H $\delta = 2.50$ ppm (1 singlet); 1H $\delta = 7.41$ ppm (1 singlet); 1H $\delta = 11.1$ ppm (very wide).

EXAMPLE 3

1-Acetoxy-2-methyl-1-pentene-3-one

A mixture of 11.4 g of 2-formyl-3-pentanone and 17 g of isopropenyl acetate was brought to reflux in the presence of 0.1 g of sulfuric acid. After removal of the acetone formed at ambient pressure, the desired product was distilled under vacuum. In this manner 11 g of 1-acetoxy-2-methyl-1-pentene-3-one was obtained under conditions of 104° C. and 16 mm of mercury, which is a yield of 70%.

NMR spectrum of the proton (CDC13): 3H towards $\delta = 1.028$ ppm (triplet); 3H towards $\delta = 1.75$ ppm (doublet); 3H towards $\delta = 2.16$ ppm (doublet); 2H towards $\delta = 2.6$ ppm (quadruplet); 1H towards $\delta = 8.14$ ppm (doublet).

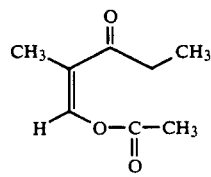

(V)

We claim:

1. 2,3,5-(4H)-trimethyl 4-pyranone having the formula:

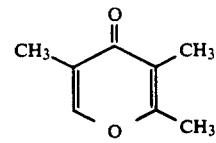

2. A process for the preparation of the compound in accordance with claim 1, comprising
acetylating a ketone derived from a 2-formyl-3-pentanone of the general formula:

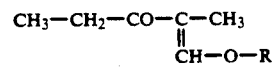

in which R designates a hydrogen atom, an alkali metal atom, an alkyl group containing from 1 to 8 carbon atoms or an acetyl radical, which may be substituted by one or more halogen atoms,
using acetic anhydride, acetyl chloride or acetyl bromide, at a temperature of between $-40°$ C. and $-30°$ C. in the presence of a Lewis acid catalyst to produce 2,3,5-(4H)-trimethyl-4-pyranone.

3. The process for the preparation of 2,3,5-(4H)-trimethyl 4-pyranone in accordance with claim 2, wherein the acetylation reaction is carried out in the presence of boron trifluoride or aluminum, cobalt or zinc halides.

4. The process for the preparation of 2,3,5-(4H)-trimethyl 4-pyranone in accordance with claim 2, wherein the acetylation reaction is carried out on 1-acetoxy-2-methyl-1-pentene-3-one.

5. 1-acetoxy-2-methyl-1-pentene-3-one having the formula:

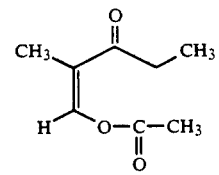

6. A process for the preparation of 2,3,5-(1H)-trimethyl 4-pyridinone having the formula:

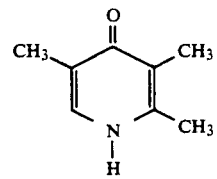

comprising subjecting a 2,3,5-(4H)-trimethyl 4-pyranone in accordance with claim 1 to an ammonolysis at between 100° C. and 150° C., under an ammonia pressure of 5 to 15 bars, in an aqueous or hydroalcoholic medium.

7. 2,3,5-(1H)-trimethyl 4-pyridinone having the formula:

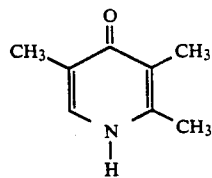

8. A process for the preparation of 2,3,5-(1H)-trimethyl 4-pyridinone comprising:

a) acetylating a ketone derived from 2-formyl-3-pentanone having the general formula:

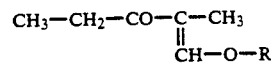

where R designates a hydrogen atom, an alkali metal atom, an alkyl group containing from 1 to 8 carbon atoms or an acetyl group using acetic anhydride, acetyl chloride or acetyl bromide, at a temperature of between −40° C. and +30° C., to obtain 2,3,5-(4H)-trimethyl 4-pyranone, and b) subjecting the 2,3,5-(4H)-trimethyl 4-pyranone obtained in step a) to an ammonolysis.

* * * * *

UNITED STATES PATENT AND TRADEMARK OFFICE
CERTIFICATE OF CORRECTION

PATENT NO.   : 5,292,885
DATED        : March 8, 1994
INVENTOR(S)  : Wirth Didier et al.

It is certified that error(s) appears in the above-identified patent and that said Letters Patent is hereby corrected as shown below:

Column 2, line 31, before "intermediate" please insert --desired--.

Column 3,    line 23, please delete "to appear"; and line 37, delete "17°C" and insert therefor --217°C--.

Column 4,    line 26, delete "-30°C" and insert therefor --+30°C--; and line 28, please delete "2,3,5-(4H)-trimethyl-4-pyranone" and insert therefor --2,3,5-(4H)-trimethyl 4-pyranone--.

Signed and Sealed this

Eleventh Day of June, 1996

Attest:

BRUCE LEHMAN

Attesting Officer    Commissioner of Patents and Trademarks